(12) United States Patent
Li et al.

(10) Patent No.: US 10,583,302 B2
(45) Date of Patent: Mar. 10, 2020

(54) GOLD WETTING ON CERAMIC SURFACES UPON COATING WITH TITANIUM HYDRIDE

(71) Applicant: Greatbatch Ltd., Clarence, NY (US)

(72) Inventors: Dongfa Li, East Amherst, NY (US); Biswa P. Das, Tonawanda, NY (US); Ashish Shah, East Amherst, NY (US)

(73) Assignee: Greatbatch Ltd., Clarence, NY (US)

( * ) Notice: Subject to any disclaimer, the term of this patent is extended or adjusted under 35 U.S.C. 154(b) by 17 days.

(21) Appl. No.: 15/712,669

(22) Filed: Sep. 22, 2017

(65) Prior Publication Data

US 2018/0085591 A1 Mar. 29, 2018

Related U.S. Application Data

(60) Provisional application No. 62/405,370, filed on Oct. 7, 2016, provisional application No. 62/398,746, filed on Sep. 23, 2016.

(51) Int. Cl.
| | |
|---|---|
| *A61N 1/375* | (2006.01) |
| *H01G 4/35* | (2006.01) |
| *H01G 4/242* | (2006.01) |
| *H01G 4/224* | (2006.01) |

(Continued)

(52) U.S. Cl.
CPC .......... *A61N 1/3754* (2013.01); *B23K 1/0016* (2013.01); *C01B 6/02* (2013.01);
(Continued)

(58) Field of Classification Search
CPC .......... A61N 1/3754; A61N 1/08; A61N 1/05; A61N 1/375; A61N 1/3758; A61N 1/3752; A61N 1/3968; H01G 2/103; H01G 4/224; H01G 2/10; H05K 5/0247; H05K 1/0213; H01R 43/00; H01R 13/5224; H01R 2201/12; B23K 35/3013; B23K 1/0016;
(Continued)

(56) References Cited

U.S. PATENT DOCUMENTS

| | | |
|---|---|---|
| 2,570,248 A | 10/1951 | Kelley et al. |
| 3,178,804 A | 4/1965 | Garibotti et al. |

(Continued)

FOREIGN PATENT DOCUMENTS

| | | |
|---|---|---|
| EP | 1796115 | 6/2007 |
| GB | 913301 | 12/1962 |

(Continued)

OTHER PUBLICATIONS

Extended European Search Report, Application No. 17192988.8, dated Jan. 24, 2018.

*Primary Examiner* — Deborah L Malamud
(74) *Attorney, Agent, or Firm* — Michael F. Scalise

(57) ABSTRACT

The application of a titanium hydride coating on a ceramic, preferably an alumina ceramic, as a facile and inexpensive approach to bond gold to the ceramic during brazing is described. During the brazing process, the deposited titanium hydride is first partially decomposed to form pure titanium intermixed with titanium hydride. The combination of pure titanium and titanium hydride contributes to improved adhesion of gold with the alumina ceramic without any detrimental reaction between pure titanium and gold. The titanium hydride coating can be applied by dip/spray/paint coating.

9 Claims, 4 Drawing Sheets

(51) Int. Cl.
*H01G 2/02* (2006.01)
*B23K 1/00* (2006.01)
*C01B 6/02* (2006.01)
*C04B 37/02* (2006.01)
*H01B 17/30* (2006.01)
*A61N 1/39* (2006.01)

(52) U.S. Cl.
CPC ......... *C04B 37/026* (2013.01); *H01B 17/301* (2013.01); *H01G 2/02* (2013.01); *H01G 4/224* (2013.01); *H01G 4/242* (2013.01); *H01G 4/35* (2013.01); *A61N 1/3968* (2013.01); *C04B 2237/125* (2013.01); *C04B 2237/343* (2013.01); *C04B 2237/403* (2013.01)

(58) Field of Classification Search
CPC ............ B23K 2101/36; B23K 35/0222; Y10T 29/49002; Y10T 29/49117; A61B 5/0031; A61B 2562/222; H01B 17/301; H01B 17/303; H01L 23/10; H01L 23/15; H01L 24/26; H01L 2924/01079
See application file for complete search history.

(56) References Cited

U.S. PATENT DOCUMENTS

| | | |
|---|---|---|
| 3,416,964 A | 12/1968 | Ignatius |
| 3,421,945 A | 1/1969 | Michalko |
| 3,681,135 A | 8/1972 | Walter et al. |
| 4,448,605 A | 5/1984 | Mizuhara et al. |
| 4,816,621 A | 3/1989 | Huebner et al. |
| 4,983,213 A | 1/1991 | Mizuhara et al. |
| 5,186,380 A | 2/1993 | Beeferman et al. |
| 5,340,012 A | 8/1994 | Beeferman et al. |
| 6,071,592 A | 6/2000 | Takahara et al. |
| 6,616,032 B1 | 9/2003 | Gasse et al. |
| 8,538,530 B1 * | 9/2013 | Orinski ................ A61N 1/3754 607/36 |
| 8,642,887 B1 | 2/2014 | Li et al. |
| 8,653,384 B2 * | 2/2014 | Tang .................... A61N 1/3754 174/650 |
| 2004/0112945 A1 | 6/2004 | Wolfgram et al. |
| 2005/0181199 A1 | 8/2005 | Shah et al. |
| 2006/0219756 A1 | 10/2006 | Tada et al. |
| 2012/0225306 A1 | 9/2012 | Zheng et al. |
| 2013/0236738 A1 | 9/2013 | Yamauchi et al. |
| 2013/0316226 A1 | 11/2013 | Adharapurapu et al. |
| 2016/0106988 A1 | 4/2016 | Koester et al. |
| 2016/0249452 A1 | 8/2016 | Terasaki et al. |

FOREIGN PATENT DOCUMENTS

| | | |
|---|---|---|
| JP | 570260 | 3/1993 |
| JP | 6100380 | 4/1994 |

* cited by examiner

GOLD WETTING ON CERAMIC SURFACES UPON COATING WITH TITANIUM HYDRIDE

CROSS-REFERENCE TO RELATED APPLICATIONS

This non-provisional patent application claims priority to U.S. Provisional Application Ser. Nos. 62/398,746, filed on Sep. 23, 2016 and 62/405,370, filed on Oct. 7, 2016.

BACKGROUND OF THE INVENTION

1. Field of the Invention

The present invention relates generally to a hermetic feedthrough terminal pin assembly, preferably of the type incorporating a filter capacitor. More specifically, this invention relates to metallizations comprising titanium for incorporation into feedthrough assemblies, particularly of the type that contain a filter capacitor and are used in implantable medical devices such as cardiac pacemakers, cardioverter defibrillators, and the like. Such feedthrough filter capacitor assemblies are designed to decouple and shield internal electronic components of the medical device from undesirable electromagnetic interference (EMI) signals. The metallization provides a surface with which a hermetic seal can be established that prevents passage or leakage of fluids through the feedthrough assembly and into the medical device.

2. Prior Art

Feedthrough assemblies are generally well known in the art for use in allowing electrical signals to pass through the housing or case of an electronic instrument. That is for electrical signals being transmitted both from the device to outside the device housing and from the outside environment to the device circuitry contained in the housing. For example, in an implantable medical device, such as a cardiac pacemaker, defibrillator, or neurostimulator, the feedthrough assembly comprises one or more conductive terminal pins supported by an insulator structure. The terminal pins act as leads for passage of electrical signals from the exterior to the interior of the medical device. The conductive terminal pins are fixed into place in passageways extending through the insulator and the insulator/terminal pin subassembly is in turn fixed into place in a ferrule. In conventional practices both of these connections are made using a metallization and gold braze process, which provides a hermetic seal between the pin and insulative material, and between the insulator and the ferrule.

Conventional metallizations used to facilitate bonding of gold to the insulative material at both the terminal pins and at the ferrule are composed of a combination of discrete layers of titanium and molybdenum or titanium and niobium. Titanium metal is commonly used as an adhesion layer to provide bonding between the insulator ceramic material, particularly that of alumina, and a different metal. However, titanium typically reacts with gold to form an intermetallic alloy. Intermetallic alloys, such as those formed by the combination of titanium and gold, can result in an undesirable brittle bond which may result in loss of hermeticity. Titanium is known to have a high diffusion coefficient in liquid gold, which increases its tendency to diffuse within gold and form these intermetallic alloy phases. Typically, when such metals are brazed, titanium can depart or lift from the surface of the insulator material and forms an intermetallic alloy with the gold braze material.

As a result, a barrier layer comprising molybdenum or niobium is applied to the outer surface of the titanium to help prevent such intermetallic alloys. The additional layer of molybdenum or niobium acts as a barrier layer to prohibit the migration of titanium from the surface of the insulator material to thereby prevent the formation of a titanium and gold intermetallic. While materials such as molybdenum and niobium typically provide adequate metallization barrier layers, they are not ideal. Molybdenum corrodes in body fluids and niobium reacts with gold (and platinum, which is a major constituent of many lead wires). Thus, both molybdenum and niobium have the potential for hermiticity failures during implant applications. Moreover, in order to retain the barrier effect and overcome the issues of corrosion and intermetallic reaction, the niobium or molybdenum layers are typically maintained at relatively high thicknesses. But, thicker barrier layers can result in residual stresses and potentially be detrimental to the integrity of the metallization layer. A thick coating also requires longer processing time and frequent coating equipment maintenance.

Consequently, recent work has been focused on an improved metallization layer through application of a titanium hydride coating as a facile and inexpensive approach to bond alumina ceramic and gold during brazing. The partial decomposition of titanium hydride to form pure titanium during the brazing process is capitalized upon to enhance wetting of gold on the alumina ceramic surface. The combination of pure titanium and titanium hydride contributes toward adhesion of gold with the ceramic without any detrimental reaction between pure titanium and gold. Moreover, a very thin layer of titanium hydride is all that is needed to promote good wetting of the gold and compact interfacial contact. The thin layer of titanium hydride can be applied by dip/spray/paint coating, with or without a binder.

SUMMARY OF THE INVENTION

The present invention relates to the application of a titanium hydride coating on a ceramic, preferably an alumina ceramic, as a facile and inexpensive approach to bond gold to the ceramic during brazing. During the brazing process, the deposited titanium hydride is first partially decomposed to form pure titanium intermixed with titanium hydride. The combination of pure titanium and titanium hydride contributes to improved adhesion of gold with the alumina ceramic without any detrimental reaction between pure titanium and gold. In that respect, the present invention relates to improved wetting of gold with an alumina ceramic through application of a relatively thin coating of titanium hydride on the ceramic. The titanium hydride coating can be applied by dip/spray/paint coating.

Preferably, at least one binder is added to the titanium hydride to help maintain the coating in place. The binder, which is preferably a combination of inorganic and organic materials in liquid form, is combined with titanium hydride powder to form a mixture that is applied to the ceramic surface and dried under ambient conditions. The relatively slow ambient drying step allows the titanium hydride particles to position in thermodynamically favorable locations and in suitable orientation, thereby reducing the risk for buildup of residual stress. This technique allows for very thin yet uniform surface coverage. The organic material decomposes completely during the initial stages of the brazing process while the inorganic binder material is retained at the gold-ceramic interface.

These and other objects and advantages of the present invention will become increasingly more apparent from a reading of the following description in conjunction with the appended drawings.

DETAILED DESCRIPTION OF THE PREFERRED EMBODIMENTS

Figure 1:
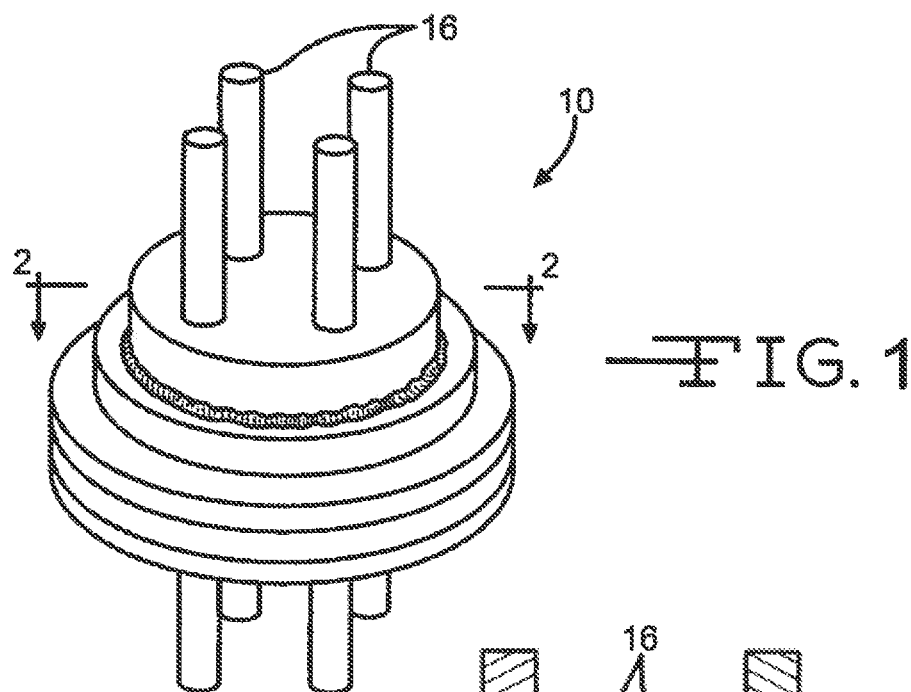
FIG. 1 illustrates a perspective view of an embodiment of a feedthrough assembly.
Figure 2:
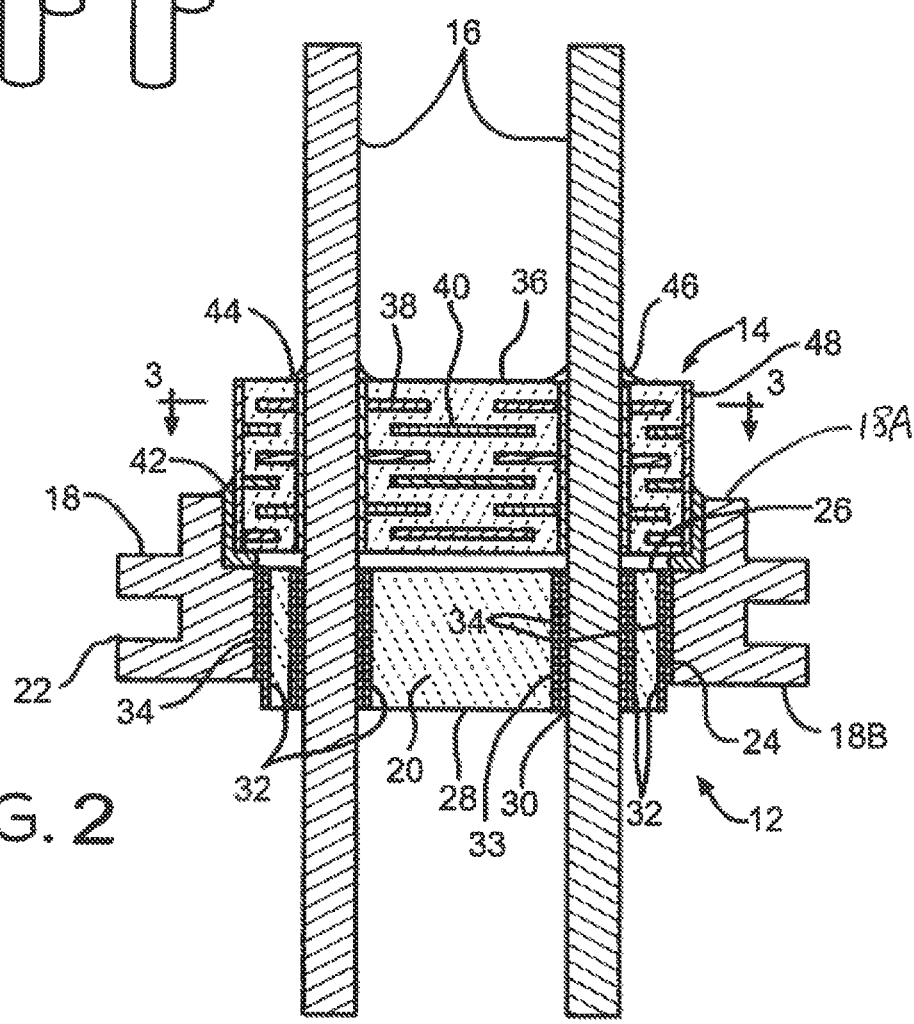
FIG. 2 shows a cross-sectional view of the feedthrough assembly taken along line 2-2 of FIG. 1.
Figure 3:
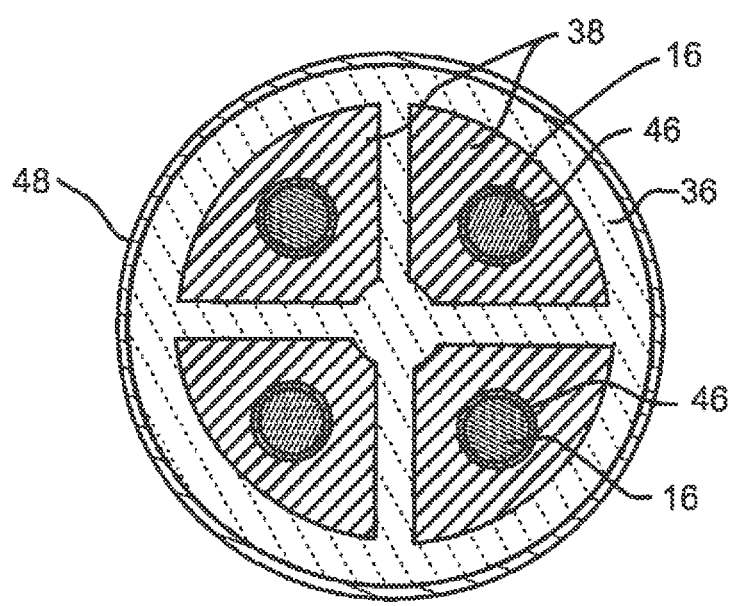
FIG. 3 illustrates a cross-sectional view of the feedthrough assembly taken along line 3-3 of FIG. 2.

Referring now to the drawings, FIGS. 1 to 3 illustrate an internally grounded feedthrough capacitor assembly 10. The feedthrough capacitor filter assembly 10 is useful with medical devices, preferably implantable devices such as pacemakers, cardiac defibrillators, cardioverter defibrillators, cochlear implants, neurostimulators, internal drug pumps, deep brain stimulators, hearing assist devices, incontinence devices, obesity treatment devices, Parkinson's disease therapy devices, bone growth stimulators, and the like.

The feedthrough capacitor assembly 10 comprises a feedthrough 12 supporting a discoidal filter capacitor 14. In an exemplary pacemaker or defibrillator, the feedthrough 12 portion of the assembly 10 includes terminal pins 16 that provide for coupling, transmitting and receiving electrical signals to and from a patient's heart while hermetically sealing the interior of the medical device against ingress of body fluids that could otherwise disrupt device operation or cause device malfunction.

The filter capacitor 14 portion of the assembly 10 serves to suppress or decouple undesirable high frequency EMI signals and noise as harmless heat energy directed to the device housing before the EMI signals can transmit down the terminal pins 16 and into the interior of the medical device. While suppressing undesirable high frequency EMI signals, the filter capacitor 14 permits relatively low frequency electrical stimulating signals and biological signals to pass unfiltered out of and into the device housing.

More particularly, the feedthrough 12 of the feedthrough filter capacitor assembly 10 comprises a ferrule 18 defining an insulator-receiving bore formed by a ferrule sidewall extending from a ferrule first end 18A to a ferrule second end 18B, the ferrule sidewall surrounding an insulator 20. Suitable electrically conductive materials for the ferrule 13 include titanium, tantalum, niobium, stainless steel, and combinations of alloys thereof, the former being preferred.

The ferrule 18 may be of any geometry, non-limiting examples being round, rectangle, and oblong. A surrounding flange 22 extends from the ferrule 18 to facilitate attachment of the feedthrough 10 to the casing (not shown) of, for example, one of the previously described implantable medical devices. The method of attachment may be by laser welding or other suitable methods.

The insulator 20 is of a ceramic material such as of alumina, zirconia, zirconia toughened alumina, aluminum nitride, boron nitride, silicon carbide, glass, or combinations thereof. Preferably, the insulating material is alumina, which is highly purified aluminum oxide. The insulator 20 has a sidewall 24 extending to a first upper side or end 26 and a second lower side or end 28. The insulator 20 is also provided with passageways 30 that receive the terminal pins 16 passing therethrough.

Non-limiting examples of terminal pins 16 include platinum, platinum alloys, particularly platinum-iridium alloys, palladium and palladium alloys. Furthermore, it is contemplated that the terminal pins 16 may comprise an exterior outer coating or layer of platinum, platinum alloys, gold, silver, palladium and palladium alloys. In that case, the core material of the terminal pins may be selected from the group consisting of niobium, tantalum, nickel-titanium (NITINOL®), titanium, particularly beta titanium, titanium alloys, stainless steel, molybdenum, tungsten, platinum, and combinations thereof. The coating may be applied through a process of sputtering, electron-beam deposition, pulsed laser deposition, plating, electroless plating, chemical vapor deposition, vacuum evaporation, thick film application methods, aerosol spray deposition, and thin cladding.

In order to facilitate hermetic attachment of the terminal pins 16 to the insulator 20 at the passageways 30 and hermetic attachment of the insulator 20 to the inner surface of the ferrule sidewall, a hermetic bond must be established between the gold braze, the insulator, and the materials of the terminal pin 16 and ferrule 18. In that respect, the present invention addresses the problem of gold being resistant to wetting of ceramic surfaces, particularly alumina ceramic surfaces.

According to the present invention, suitable gold wetting is accomplished at the respective alumina ceramic surfaces (outer insulator sidewall surface 24 adjacent to the ferrule 18 and at the insulator surface defining the terminal pin passageways 30) by application of a titanium hydride coating on the ceramic. As shown in FIG. 2, a coating 32 of titanium hydride is applied to the insulator sidewall 24 and to a sidewall 33 of the terminal pin passageways 30 to facilitate hermetic sealing of the braze material 34 to the ferrule 18 and the outer sidewall 24 of the insulator 20 and to the terminal pins 16 and the passageway sidewall 33, respectively.

Figure 4:
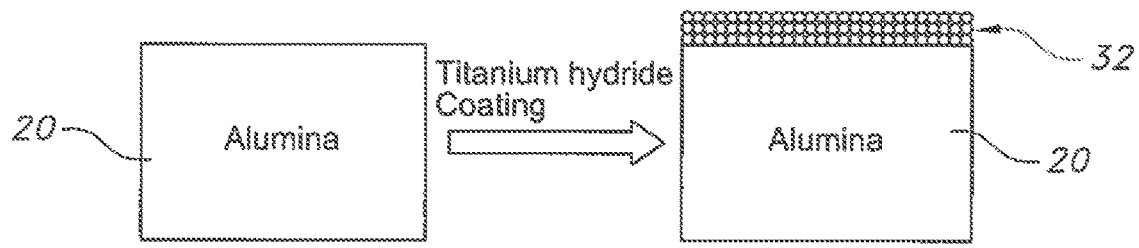
FIG. 4 is a schematic representation of a titanium hydride coating 32, with or without binder, contacting an insulator 20.

Specifically, FIG. 4 is a schematic drawing showing that the titanium hydride coating 32 applied to the alumina insulator 20 comprises at least two layers of titanium hydride, and preferably three or more up to about ten layers of titanium hydride (three layers are depicted). This drawing is intended to schematically depict the coating 32 of the titanium hydride layers that are applied to the insulator sidewall 24 and to the sidewall 33 of the terminal pin passageways 30 shown in FIG. 2, That is for the purpose of aiding the gold braze material 34 in hermetically sealing to the ferrule 18 and the outer sidewall 24 of the insulator 20 and to the terminal pins 16 and the sidewall 33 of the insulator passageways, respectively.

It is known that at high temperatures titanium hydride begins decomposing under vacuum to form titanium and liberate hydrogen. In that respect, it is an important aspect of the present invention that a suitable coating 32 applied to the alumina insulator surface or surfaces that are intended to support a gold brass comprise at least two layers of titanium hydride. In a single layer application all of the titanium hydride particles are on the insulator surface and are very susceptible to complete decomposition. For that reason, at least two layers of titanium hydride are desired for the coating 32. A preferred titanium hydride powder for use in hermetic seals for feedthroughs intended for incorporation into implantable medical devices has a 200 mesh size, which equates to a diameter of about 74 µm. Hence, the lowest preferred thickness of the coating 32 is about 148 µm, which represents two layers of the 200 mesh material. However, there is an upper limit to the thickness of the titanium hydride coating 32. Coating that have greater than about ten layers (about 1,000 µm thick) can result in diffusion of gold into the titanium hydride without any wetting of the underlying alumina ceramic. So, a suitable coating 32 thickness is preferably greater than zero, but less than 1,000 µm thick. It is hypothesized that at greater coating thicknesses, the amount of pure titanium converted from titanium hydride is sufficient to diffuse the gold before a sufficient amount of gold can contact the alumina ceramic substrate.

A simple, efficient and inexpensive technique to obtain the desired coating 32 is to prepare a mixture of titanium hydride powder and a liquid binder, which can be either an organic or inorganic binder, or a combination thereof. Preferred organic binders are polyethylene glycol and methyl cellulose. Suitable inorganic binders are colloidal silica and sodium silicate aqueous dispersions. While preferred, the binder is not necessary in order to practice the present invention.

As shown in FIG. 4, a very thin coating 32 of the binder/titanium hydride mixture (three layers are shown, but two layers will suffice) is sufficient to obtain good wetting and a compact interface between gold 34 and the alumina insulator 20. The titanium hydride is preferably applies to the insulator 20 by one of dip coating, spray coating and paint coating, with or without the binder. Before heat decomposition of the titanium hydride coating 32 begins, however, the coated insulator 20 serving as a substrate is allowed to dry under ambient conditions. The slow ambient drying step allows the titanium hydride particles to locate in thermodynamically favorable positions and in suitable orientations, thereby reducing the risk for buildup of residual stress.

Figure 5:
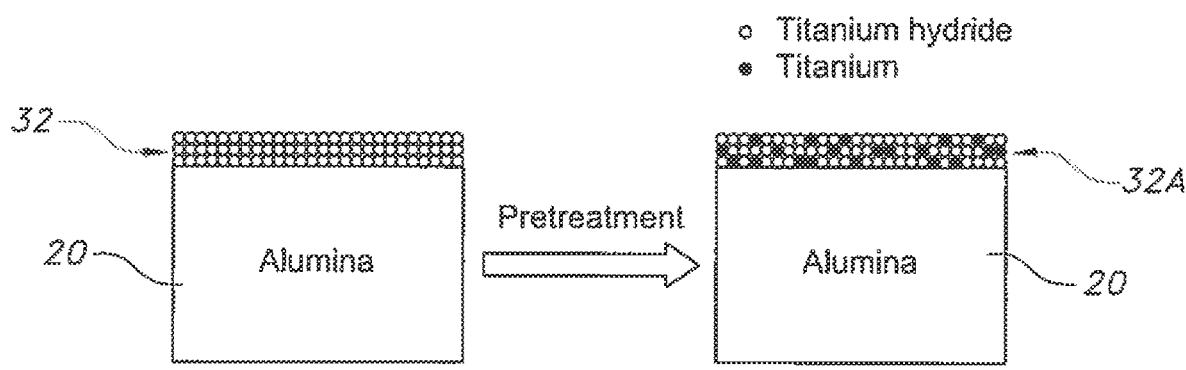
FIG. 5 is a schematic representation of a pretreatment step where the titanium hydride coating 32 shown in FIG. 4 has partially decomposed to form a coating 32A comprising titanium hydride (open circles) and titanium (closed circles).

As schematically depicted in FIG. 5, an exemplary brazing protocol according to the present invention includes a pretreatment step where the titanium hydride coating 32, with or without binder, is heated at 750° C. for 30 minutes in a vacuum of $10^{-7}$ Torr. An alternate pretreatment protocol includes heating the titanium hydride coating 32, with or without binder at 900° C. for 40 minutes in a vacuum of $10^{-7}$ Torr. Both pretreatment methods result in partial decomposition of titanium hydride to thereby provide a coating 32A comprising titanium (closed circles) intermixed with titanium hydride (open circles). The combination of pure titanium mixed with titanium hydride in the coating 32A allows for good wetting of gold 34 so that a strong gold-alumina braze is obtained.

In a broader sense, titanium hydride decomposes at about 400° C. so any temperature greater than that is expected to result in partial decomposition of the titanium hydride coating 32 to form the coating 32A of titanium (closed circles) intermixed with titanium hydride (open circles). Preferably, the titanium hydride coating 32 is heat treated at a temperature ranging from about 400° C. to about 1,000° C. for about 30 to about 180 minutes. Suitable vacuum pressures range from $10^{-1}$ Torr to $10^{-9}$ Torr. Moreover, while the present invention is described for use with an alumina ceramic insulator, that should not be seen as a limitation. Broadly, in addition to an alumina ceramic, the present invention is intended for use with any of the previously described insulator materials including aluminum nitride, boron nitride, silicon carbide, glass, or combinations thereof.

Figure 6:
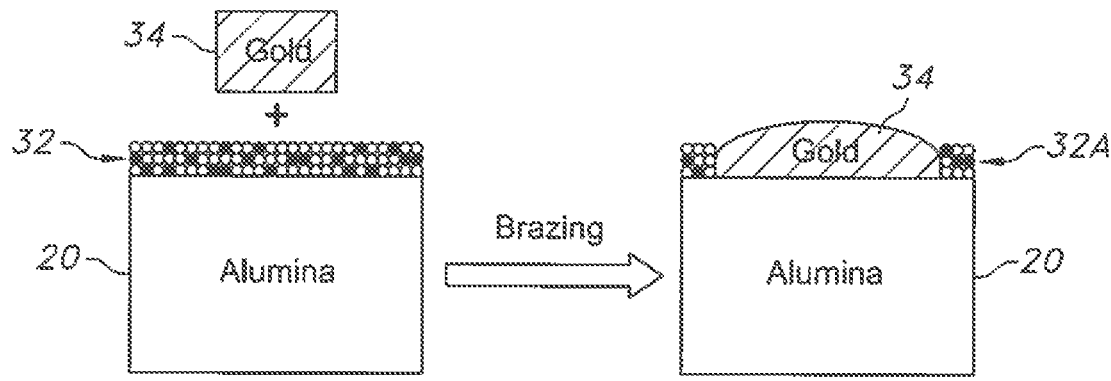
FIG. 6 is a schematic representation of gold 34 brazed to the titanium hydride coated insulator 20 according to the invention.

FIG. 6 schematically depicts the brazing process where gold 34 is melted and contacts the insulator (alumina) substrate 20 in a hermetic bond. In practice, a first gold fillet in the shape of a gold ring is positioned in a surrounding relationship with the insulator outer surface adjacent to the ferrule opening. A second gold fillet in the shape of a gold ring is positioned in a surrounding relationship with the terminal pin adjacent to the insulator passageway to thereby construct a feedthrough sub-assembly. Gold melts at 1,064° C., prior to attachment of the filter capacitor 14, this feedthrough sub-assembly is heated to at least that temperature to affect a suitable hermetic bond at the insulator/ferrule and at the insulator/terminal pin. If organic binders are present with the titanium hydride, they decompose. If the binders are inorganic, except for liberation of water, they remain behind. A hermetic seal according to the present invention where gold 34 contacts the ferrule 18 and the outer sidewall 24 of the insulator 20 and contacts the terminal pins 16 and the passageway sidewall 33, respectively, as shown in FIG. 2, is defined as a helium leak rate that is no more than $10^{-7}$ cubic centimeters per second.

Figure 7:
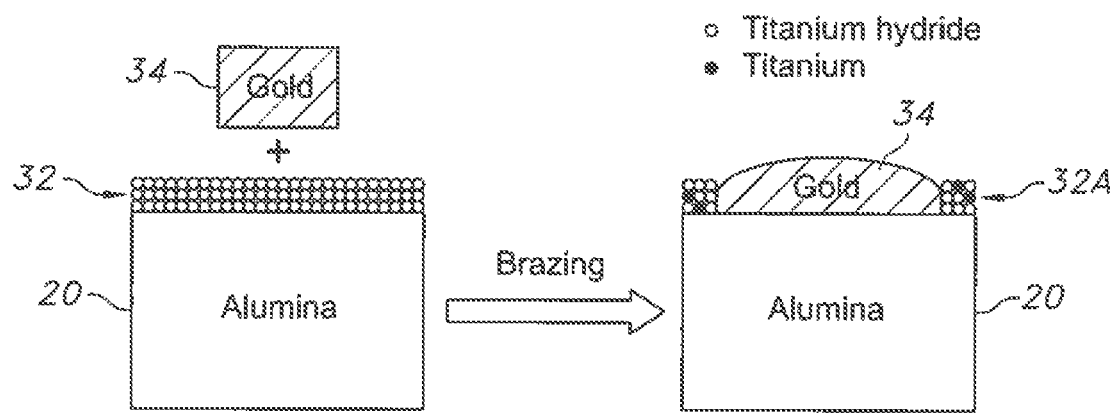
FIG. 7 is a schematic representation of gold 34 brazed to the titanium hydride coated insulator 20 according to an alternate embodiment of the present invention.

FIG. 7 schematically depicts a second embodiment according to the present invention where gold 34 is brazed directly onto the titanium hydride coating 32 supported on the alumina insulator 20 serving as a substrate. As described above, a first gold fillet in the shape of a gold ring is positioned in a surrounding relationship with the insulator outer surface adjacent to the ferrule opening. A second gold fillet in the shape of a gold ring is positioned in a surrounding relationship with the terminal pin adjacent to the insulator passageway to thereby construct a feedthrough sub-assembly. Then, during brazing where the temperature is increased linearly or step-wise to at least 1,064° C., partial decomposition of the titanium hydride coating 32 to form pure titanium intermixed with titanium hydride takes place under the gold, which allows for direct wetting of the gold onto the alumina ceramic surface 20.

Thus, after brazing is completed, the braze profile comprises the partially decomposed titanium hydride coating having intermixed titanium and titanium hydride contacting the alumina ceramic surface. Gold in turn is bonded to the mixture of titanium and titanium hydride opposite the alumina ceramic. In other words, the finished braze assembly has the following profile: alumina ceramic/titanium and titanium hydride mixture/gold/metal of ferrule or of terminal pin. If binders are used in the titanium hydride coating, residual inorganic binders, but not organic binders, are also present in the titanium and titanium hydride mixture. The present braze profile is in contrast to a prior art braze having the following profile; alumina ceramic/titanium adhesion layer/barrier layer (molybdenum or niobium)/gold/metal of the ferrule or terminal pin.

Referring back to FIGS. 1 to 3, if the feedthrough capacitor assembly 10 is intended for incorporation into implantable medical devices such as cardiac pacemakers, cardioverter defibrillators, and the like, which will be used in the presence of high frequency EMI signals, the previously described filter capacitor 14 is attached to the feedthrough 12. The filter capacitor 14 provides for filtering undesirable EMI signals before they can enter the device housing via the terminal pins 16 and comprises a ceramic or ceramic-based dielectric monolith 36 having multiple capacitor-forming conductive electrode plates supported therein. The capacitor dielectric 36 preferably has a circular cross-section matching the cross-section of the ferrule 18 and supports a plurality of spaced-apart layers of first or "active" electrode plates 38 in spaced relationship with a plurality of spaced apart layers of second or "ground" electrode plates 40. The filter capacitor 14 is preferably joined to the feedthrough 12 adjacent to the insulator side 26 by an annular bead 42 of conductive material, such as a solder or braze ring, or a thermal-setting conductive adhesive, and the like. The dielectric 36 includes lead passageways 44 provided with an inner surface metallization layer. The terminal pins 16 pass through lead passageways 44 and are conductively coupled to the active plates 38 by a conductive braze material 46 contacting between the terminal pins 16 and the bore metallization. In a similar manner, the ground plates 40 are electrically connected through an outer surface metallization 48 and the conductive material 42 to the ferrule 18.

Although several embodiments have been described in detail for purposes of illustration, various modifications may be made to each without departing from the scope and spirit of the invention. Accordingly, the invention is not to be limited, except as by the appended claims.

What is claimed is:

1. A hermetic feedthrough for an implantable medical device, the feedthrough comprising:
    a) a ferrule defining a ferrule opening, wherein the ferrule is configured to be attachable to an opening in a housing of an implantable medical device;
    b) an insulator at least partially residing in the ferrule opening where a first gold braze hermetically seals an outer sidewall of the insulator to the ferrule, wherein at least one insulator passageway defined by an insulator inner surface extends through the insulator to an insulator first end surface and an insulator second end surface; and
    c) an electrically conductive terminal pin residing in the at least one insulator passageway where a second gold braze hermetically seals the terminal pin to the insulator,
    d) wherein at least one of the first and second gold brazes has the following respective braze profile:
        A) the insulator outer sidewall contacting a titanium and titanium hydride mixture layer contacting gold contacting the ferrule; and
        B) the insulator inner surface contacting a titanium and titanium hydride mixture layer contacting gold contacting the terminal pin, and
    e) wherein, in the braze profile for at least one of the first and second gold brazes, the titanium and titanium hydride mixture layer includes at least one residual inorganic binder selected from colloidal silica and sodium silicate.

2. The feedthrough of claim 1, wherein, in the braze profile for at least one of the first and second gold brazes, the titanium hydride has a 200-mesh size or a diameter of about 74 μm.

3. The feedthrough of claim 1, wherein, in the braze profile for at least one of the first and second gold brazes, the titanium and titanium hydride mixture layer has a thickness of from about 148 μm to about 1,000 μm.

4. The feedthrough of claim 1, wherein, in both the first and second gold braze profiles, there is a titanium and titanium hydride mixture layer that includes at least one residual inorganic binder selected from colloidal silica and sodium silicate.

5. The feedthrough of claim 1, wherein, in the braze profile for at least one of the first and second gold brazes, the titanium and titanium hydride mixture layer has a thickness that is greater than zero, but less than about 1,000 μm.

6. The feedthrough of claim 1, wherein the ferrule is selected from the group consisting of titanium, tantalum, niobium, stainless steel, and combinations of alloys thereof.

7. The feedthrough of claim 1, wherein the insulator is selected from the group consisting of an alumina ceramic, aluminum nitride, boron nitride, silicon carbide, glass, and combinations thereof.

8. The feedthrough of claim 1, wherein the terminal pin is selected from the group consisting of platinum, platinum-iridium alloys, palladium, and palladium alloys.

9. The feedthrough of claim 1, wherein the terminal pin extends from a terminal pin first portion to a terminal pin second portion, and wherein the terminal pin first portion extends outwardly beyond the insulator first end surface and the terminal pin second portion extends outwardly beyond the insulator second end surface.

* * * * *